United States Patent [19]

O'Brien, Jr. et al.

[11] 4,298,591
[45] Nov. 3, 1981

[54] INSTANTANEOUS RADIOIODINATION OF ROSE BENGAL AT ROOM TEMPERATURE AND A COLD KIT THEREFOR

[75] Inventors: Harold A. O'Brien, Jr., Los Alamos, N. Mex.; Homer B. Hupf, Sausolito, Calif.; Philip M. Wanek, Los Alamos, N. Mex.

[73] Assignee: The United States of America as represented by the United States Department of Energy, Washington, D.C.

[21] Appl. No.: 26,509

[22] Filed: Apr. 3, 1979

[51] Int. Cl.³ .................... A61K 49/00; A61K 43/00; G01T 1/00; B65D 71/00
[52] U.S. Cl. .................................... 424/1; 422/61; 424/9
[58] Field of Search .................... 424/1, 9; 422/61

[56] References Cited

U.S. PATENT DOCUMENTS

| | | | |
|---|---|---|---|
| 3,743,713 | 7/1973 | Kato et al. | 424/1 |
| 3,928,552 | 12/1975 | Winchell et al. | 424/1 |
| 3,959,455 | 5/1976 | Ansari et al. | 424/1 |
| 4,028,389 | 6/1977 | Wenzel et al. | 424/1 |

OTHER PUBLICATIONS

Rabin et al., Int. J. Appl. Rad. Isotopes, 19, 361–367 (1968).
Serafini et al., J. Nucl. Med., 16, 629–632 (1975).
Ginzburg, Chem. Abstracts, vol. 79, No. 19, Nov. 12, 1973, Abstract #112910j.
Brousil et al., Chem. Abstracts, vol. 79, No. 5, Aug. 6, 1973, Abstract #29411b.

*Primary Examiner*—Padgett, Benjamin R.
*Assistant Examiner*—Christine M. Nucker
*Attorney, Agent, or Firm*—Robert W. Weig; Paul D. Gaetjens; James E. Denny

[57] ABSTRACT

The disclosure relates to the radioiodination of rose bengal at room temperature and a cold-kit therefor. A purified rose bengal tablet is stirred into acidified ethanol at or near room temperature, until a suspension forms. Reductant-free $^{125}I^-$ is added and the resulting mixture stands until the exchange label reaction occurs at room temperature. A solution of sterile isotonic phosphate buffer and sodium hydroxide is added and the final resulting mixture is sterilized by filtration.

12 Claims, 1 Drawing Figure

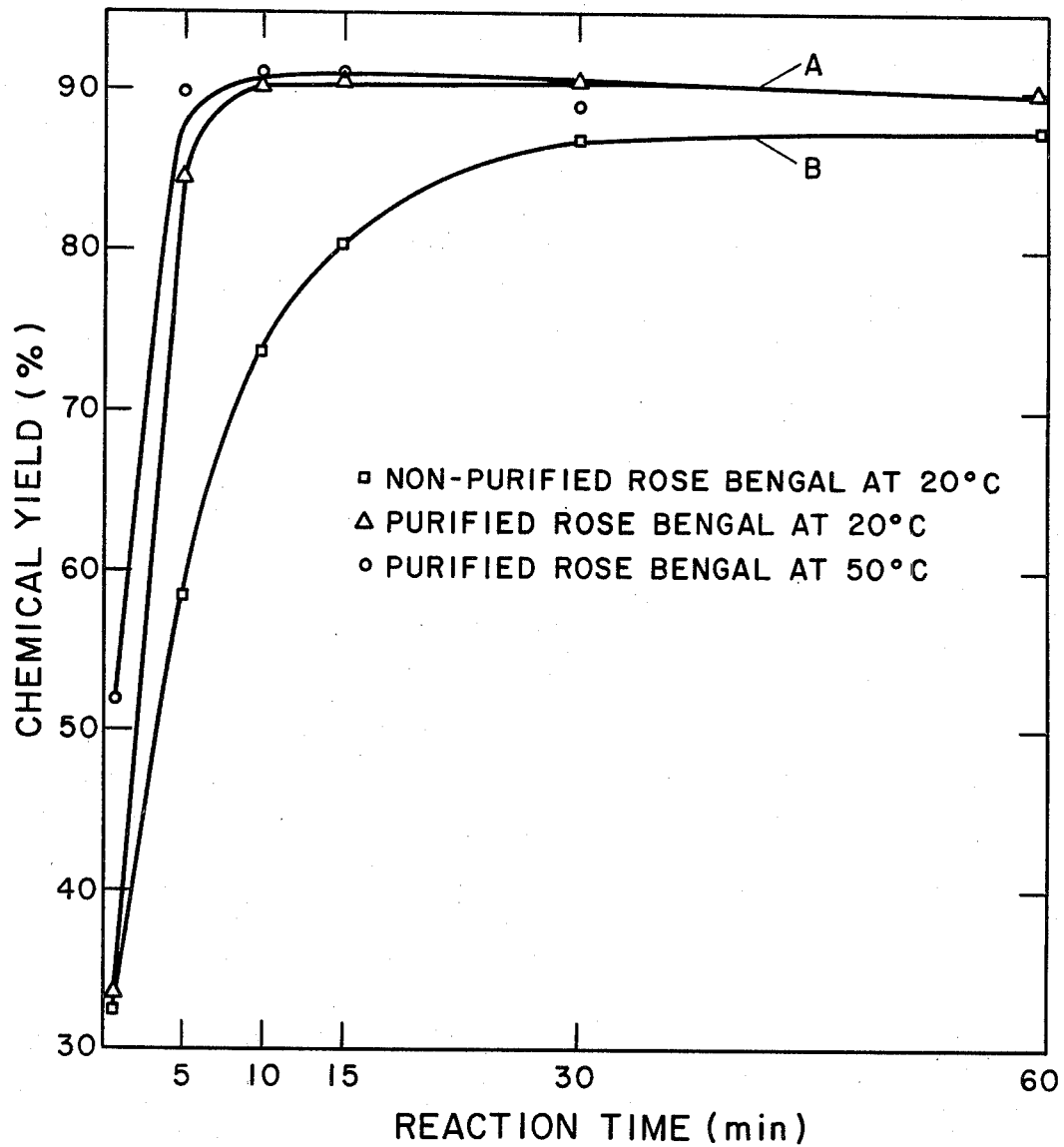

INSTANTANEOUS RADIOIODINATION OF ROSE BENGAL AT ROOM TEMPERATURE AND A COLD KIT THEREFOR

FIELD OF THE INVENTION

The invention relates to the field of nuclear medicine, nuclear pharmacy and radioisotopes, and more particularly, to the use of iodine-123 in hepatobiliary diagnostic tests.

BACKGROUND OF THE INVENTION

I-131 rose bengal has been a valuable diagnostic agent for hepatobiliary tests but its use has declined recently from concern over absorbed radiation dose from the I-131 as well as inefficient detection of the 364-keV I-131 photon with a gamma camera. Rose bengal labeled with I-123 does not have these drawbacks and has been evaluated in a limited clinical study which concluded that the larger photon flux from larger permissible amounts of the I-123 agent would prove advantageous in the differentiation between hepatocellular and extrahepatic obstructive jaundice. This study was reported in the Journal of Nuclear Medicine, July, 1975, Vol. 16, No. 7, pages 629–632, and was authored by A. N. Serafini et al.

The 13 hour half life of I-123 presents a problem to users unless the period from the end of production to clinical administration is sufficiently short. This problem can be minimized by the utilization of cold kits and the present invention provides such a cold kit.

The present methods of preparing radioiodinated rose bengal require temperatures from between 50°–120° C. and reaction times of 1 hour or more. Representative methods are revealed by P. Rabin et. al., "A New Method of Labelling Rose Bengal With I-131 or I-125," International Journal of Applied Radiation Isotopes, 19, pp. 361–367, 1968 and A. A. Sunar et. al., "Preparation of Iodine-131 Labeled Rose Bengal," Radiochemical Acta, 12, 119, 1969.

SUMMARY OF THE INVENTION

In accordance with the present invention, there is provided a method of labeling rose bengal rapidly in an acidified ethanol solution at a convenient temperature such as room temperature, typically about 20° C. There is also provided a cold kit for use in hospitals, clinics and the like, with which one may radioiodinate rose bengal at room temperature in about 15 minutes.

DETAILED DESCRIPTION OF THE INVENTION

The invention comprises a method of radioiodinating rose bengal. The invention can be carried out within a temperature range of 15° C. to 50° C., preferably between about 15° C. and about 25° C. because room temperature is usually the most convenient temperature for an individual or a few persons to manually perform a process in a hospital or medical laboratory. Room temperature usually lies between 15° C. and 25° C. That the invention can be carried out at room temperature is an advantage of the invention.

Rose bengal is placed in acidified ethanol. In carrying out the preferred embodiment the rose bengal is purified because a medical use is contemplated and because of the enhanced labeling yield. In the cold kit a tablet of purified rose bengal plus $KIO_3$ is used because a tablet is easy to sanitarily package and use. The rose bengal and oxidizing agent could also be packaged by freeze drying techniques. An oxidizing agent, such as $MnO_2$, $KMnO_4$, or $KIO_3$, is added to the tablet to effect the conversion of radioiodide to radioiodine. The preferred oxidizing agent is $KIO_3$ because of its known compatibility with rose bengal. Relative to the amount of iodide present, the quantity of oxidizing agent added should be at least that required to maintain stoichiometry or an excess. The optimum amount of added $KIO_3$ ranges from about 0.225 mg to about 0.450 mg, when the iodide amounts to $10^{-7}$ to $10^{-9}$ molar. The preferred amount of $KIO_3$ is approximately 0.300 mg.

The ethanol can be acidified with acids such as hydrochloric, sulfuric, and phosphoric; the preferred acid being hydrochloric. The pH should be less than 2.5, and preferably between about 1.0 and about 2.0. The solution is stirred until a uniform suspension forms.

Radioactive iodide is added to the rose bengal-acidified ethanol-$KIO_3$ solution. A reductant-free iodide solution is preferred because the presence of reducing agents counteracts the oxidizing ability of the $KIO_3$. However, the radioiodination of rose bengal will occur even in the presence of reducing agents as long as a sufficient excess of $KIO_3$ is added to the reaction mixture. Any isotope or combination of isotopes of iodine may be used. However, in the preferred embodiment, $^{123}I^-$ is utilized because its half-life, photon energy, and absence of particulate emission characteristics are desirable for the radio pharmaceutical use contemplated. $^{125}I^-$ and $^{131}I^-$ are also useful isotopes in that $^{125}I^-$ is useful in labeling technology and $^{131}I^-$ is useful as a diagnostic agent as well as in labeling. It will be appreciated by those skilled in the art that other isotopes of iodine can be utilized in practicing the invention and that the invention is not limited to the use of any specific isotope or isotopes.

The resulting mixture stands for a time sufficient to allow the exchange label reaction to occur, typically at room temperature, for about fifteen minutes. This relatively fast reaction time is one of the notable advantages of the invention.

A solution of sterile isotonic buffer, such as citrate, phosphate, barbital, or acetate, and sodium hydroxide are then added to place the mixture of the invention into solution for intravenous use and to adjust the pH of the solution to between 6.9 and 7.5. In the preferred embodiment, phosphate buffer is utilized. The purpose of the pH range being adjusted to between 6.9 and 7.5 is to make the invention more compatible with the living biological system into which it will be introduced.

The solution is then sterilized by any of a number of means, such as membrane sterilization, ultra violet light, dry heat or autoclaving, so that it may be medically used, i.e., introduced into a living body.

To practice the invention, one need not use purified rose bengal, reductant-free sodium iodide or any one particular isotope of iodine. However, commercially available rose bengal is typically insufficiently pure for pharmaceutical use as a hepatobiliary agent which is the preferred use of the resulting mixture. Therefore, in the examples, the rose bengal was purified by precipitation from a 10 mg/ml solution in ethanol by the addition of an equal volume of 1 M hydrochloric acid followed by centrifugation, removal of the supernate, and a water wash. The purity of rose bengal was demonstrated by visible absorption spectroscopy analysis performed in the 480–600 nm range.

EXAMPLE 1

Ten milligrams of purified rose bengal dissolved in 2 ml nondenatured ethanol, along with 0.2 ml of 1.5-mg/ml potassium iodate and 0.06 ml 1 M hydrochloric acid, were placed in a 10-ml serum vial, which was then stoppered and crimp-sealed. Using a 1-ml syringe and needle, 200 to 600 µCi of reductant-free sodium iodide [$^{125}$I] was added in a maximum volume of 0.3 ml. Samples of 0.2 ml were removed from the vial at 30 sec, 5, 10, 15, 30, and 60 minutes following the addition of the radioactivity and placed in a microcentrifuge tube. The rose bengal was precipitated in each sample by the addition of 0.2 ml 1 M hydrochloric acid, centrifuged, and the supernatant placed in a similar centrifuge tube. Each precipitate was resuspended in 0.2 ml water, centrifuged, and the wash added to the first supernate. The rose bengal precipitate was dissolved in 0.5 ml phosphate buffer, pH 7.3. Each set of product and supernate plus wash was assayed for radioactivity to determine the chemical yield of product. To determine the total labeling yield, reaction chromatograms were performed on the 10- and 15-minute samples before precipitation, using ascending paper-strip chromatography in an aqueous solution of 3% ammonium hydroxide plus 25% ethanol. The $R_f$ values of rose bengal, iodine and iodide were found to be 0.64, 0.96, and 0.96, respectively. Iodine is apparently converted to iodide in this chromatographic solvent, so iodine and iodide have the same $R_f$ value. This point was confirmed by preparing duplicate reaction samples containing no rose bengal and performing the chromatography both in 3% ammonium hydroxide plus 25% ethanol and in 85% methanol. One radioactive peak was found in the rose bengal solvent at $R_f$ 0.96 and two peaks were observed in the methanol solvent with $R_f$ values corresponding to iodine and iodide. $R_f$ values in 85% methanol were previously determined to be ~0 and 0.82 for iodine and iodide respectively. The reaction procedures described above were performed in triplicate at 20° C., 50° C., and 92° C. to study the effect of temperature. In addition, a triplicate set of experiments was performed as described at 20° C. using nonprepurified rose bengal.

Biologic confirmation of the movement of the labeled product through the hepatobiliary system was obtained in a Rhesus monkey. The labeled product was prepared in a Wheaton-Hopkins tagging vial to facilitate aseptic preparation during the precipitation and water-washing steps, in addition to showing that the concurrent removal of ethanol and free radioiodide could be achieved in a single vial. The results of the product thus prepared were compared with results in a similar test on the same monkey using commercially-available I-131 rose bengal. In each case, the monkey was injected with a solution containing approximately 270 µCi of I-131-labeled product and less than 1 mg rose bengal. The monkey was imaged at 20, 80, and 100 minute postinjection with a rectilinear scanner equipped with an I-131 collimator.

EXAMPLE 2

A true solution is not required to achieve high labeling yield. Therefore, a wafer tablet containing purified rose bengal and KIO$_3$ was formulated to test the feasibility of a simplified and more rapid method of preparation with a subsequent reduction of the amount of ethanol required. Using a stainless steel tablet mold 0.04 cm thick, 18-20 tablets each weighing from 8.8 to 11.0 mg (9.4 mg, average) were manufactured by spatulating 250 mg of purified rose bengal powder with 0.25 ml of KIO$_3$ (75 mg/ml). Upon reaching a smooth paste with the desired consistency, the mass was molded.

A dried wafer was placed in a 10-ml rubber-stoppered serum vial together with a Teflon-coated magnetic stirring bar. Six hundred µl of acid-alcohol solution (1.0 M HCl and ethanol, 1:11 v/v) were added through the septum and the mixture stirred until a uniform suspension was produced; this was followed by the addition of 200–600 µCi of reductant-free $^{125}$I$^-$. On an atom-per-atom basis, 600 µCi of carrier-free $^{125}$I$^-$ used in this study contains approximately 7 times the number of iodine atoms that would be contained in 10 mCi of carrier-free $^{123}$I. The mixture was allowed to stand for 15 minutes at room temperature ~20° C. A solution of 4.2 ml of sterile isotonic phosphate buffer (0.15 M) plus 0.06 ml of 1 M NaOH was then added, giving a final product at pH 7.5. The product can be aseptically prepared with terminal sterilization by Millipore ® filtration. Aliquots of the final products were chromatographed, passed through the molecular sieve, examined by visible spectroscopy, and subjected to sterility testing.

The impurity found in the rose bengal starting material was observed to reduce the overall labeling yield of the rose bengal product. After 15 minutes of reaction time at room temperature ~20° C., the chemical yield of the labeled rose bengal averaged only 80.5%; whereas, using the purified starting material, the rose bengal yields following precipitation and washing, averaged 91.1% after 15 minutes in both the 20° C. and the 50° C. tests, and showed no further increase with time. The FIGURE shows the product yields as a function of time. Curve A is the average yield of three determinations at 20° C. using nonpurified rose bengal. The experimental data are presented in the Table. Results of the 92° C. studies are not shown for reasons explained below.

Reaction chromatograms, indicating the labeling reaction yield before precipitation and wash, showed less than 5% free iodine and iodide for all 20° C. and 50° C. samples taken at 15 minutes after addition of the radioactivity. Reaction chromatograms of the labeling performed at 92° C. showed an additional colored spot, $R_f$ 0.75, which contained 10% of the radioactivity after 15 minutes and ~50% of the activity after 60 minutes. The chromatograms also demonstrated more than 10% free iodide. Aliquots of products from the boiling-water reaction (92° C.) were separated by molecular filtration and examined for absorbance peaks as described earlier.

TABLE

CHEMICAL YIELDS OF LABELED ROSE BENGAL AT 20 AND 50° C.

| | Yield percentage at indicated reaction time (min) | | | | | |
|---|---|---|---|---|---|---|
| | 0.5 | 5 | 10 | 15 | 30 | 60 |
| Prepurified rose bengal, 20° C. | 33.3 | 82.6 | 87.5 | 90.9 | 87.5 | 90.6 |
| | 54.2* | 86.9 | 91.3 | 91.6 | 87.5 | 87.5 |
| | 63.6+ | 83.3 | 91.7 | 91.7 | 91.3 | 91.3 |
| Average | — | 84.3 | 90.2 | 91.4 | 88.0 | 89.8 |
| Prepurified rose bengal, 50° C. | 51.7 | 86.8 | 89.8 | 89.8 | 88.0 | 86.6 |
| | 73.9* | 91.3 | 91.3 | 91.6 | 91.3 | 90.8 |
| | 91.3+ | 91.6 | 91.3 | 91.6 | 91.3 | 90.8 |
| Average | — | 89.9 | 90.8 | 90.9 | 90.0 | 89.4 |
| Nonprepurified rose bengal, | 36.2 | 60.0 | 77.5 | 84.3 | 88.6 | 86.1 |
| | 31.5 | 61.8 | 76.9 | 81.0 | 85.0 | 91.1 |

TABLE -continued
CHEMICAL YIELDS OF
LABELED ROSE BENGAL AT 20 AND 50° C.

| | Yield percentage at indicated reaction time (min) | | | | | |
|---|---|---|---|---|---|---|
| | 0.5 | 5 | 10 | 15 | 30 | 60 |
| 20° C. | 29.8 | 53.9 | 66.6 | 76.2 | 87.3 | 85.5 |
| Average | 32.5 | 58.5 | 73.6 | 80.5 | 86.9 | 87.5 |

*1-min reaction time.
+1.5-min reaction time.

Three fractions having absorbance peaks at 532, 542, and 545 nm were separated, and none corresponded to the 548–550 nm absorbance peak of tetrachlorotetraiodofluorescein. Despite the fact that the peak activity on the chromatographic strip occurred at an $R_f$ value corresponding to that of rose bengal, we are convinced by the visible spectroscopy data that rose bengal was no longer present. Thus, since the labeled product at 92° C. was not rose bengal, the product yield as a function of time could not be presented.

Molecular filtration of aliquots of the final products prepared at 20° C. and 50° C. both indicated one fraction with an absorbance peak at 550 nm.

Losses in processing time and overall chemical yield associated with rose bengal precipitation, washing, and resuspension encountered in the Wheaton-Hopkins vial method prompted a study of a procedure employing a wafer tablet of purified rose bengal and $KIO_3$. Several separate experiments were performed at room temperature ($\sim 20°$ C.) for 15 minutes, and chromatograms of the final products showed only 3–7% free $^{125}I-$, which is within the limit of 10% established by the United State Pharmacopia. Molecular filtration and absorbance studies showed the products from all these experiments to be of one fraction having absorbance peaks in the 548–550 nm range, which has been shown to correspond to that of pure rose bengal.

The rose bengal potassium iodate tablets appear to be chemically stable for a period of at least 21 days. No degradation of I-125 labeled rose bengal has been observed in a 72 hour period which is the most probable time period within which one expects an I-123 labeled product to be utilized.

It is essential that the radioactive iodide solution utilized in practicing the invention be free of reducing agents; otherwise the role of the potassium iodate will be inhibited and diminished yields of labeled rose bengal will result.

With this new procedure, which is adaptable to a cold kit preparation, the labeling of the rose bengal can be performed in the clinical unit by a trained technologist, using reductant- and carrier-free, high concentration $Na^{123}I$. Thus greater economy can be realized, since decay losses between end of bombardment and clinical administration of the iodine-123 would be substantially reduced.

What we claim is:

1. A method for radioiodinating rose bengal comprising the steps of:
   placing rose bengal and a suitable oxidizing agent in acidified ethanol;
   stirring the solution resulting until it forms a uniform suspension;
   adding an iodide in which the iodine moiety is radioactive; and
   allowing the resulting mixture to stand for a time sufficient for the exchange label reaction to occur.

2. The invention of claim 1 wherein the iodine moiety used comprises $^{123}I-$.

3. The invention of claim 1 wherein the iodine moiety used comprises $-^{125}I-$.

4. The invention of claim 1 wherein the iodine moiety used comprises $-^{131}I-$.

5. The invention of claim 1 wherein the iodide is reductant free.

6. The invention of claim 1 wherein the oxidizing agent comprises $KIO_3$.

7. The invention of claim 1 further comprising, after the exchange label reaction occurs, adding a solution of sterile isotonic phosphate buffer and sodium hydroxide and terminally sterilizing the resulting mixture.

8. The invention of claim 7 wherein terminal sterilization is accomplished by membrane filtration.

9. The invention of claim 7 wherein the pH of the sterile isotonic phophate buffer and sodium hydroxide is between about 6.9 and about 7.5.

10. The invention of claim 1 wherein the label exchange mixture standing time is at least about fifteen minutes.

11. A cold kit for radioiodinating rose bengal at room temperature comprising:
    a packaged composition of purified rose bengal and $KIO_3$, and a stirring bar contained in a sterilized, sealed serum vial;
    a separately packaged solution of acidified ethanol; and
    a separately packaged measured solution of sterile phosphate buffer and sodium hydroxide solution in a sealed serum vial.

12. The invention of claim 11 wherein said stirring bar comprises a tetrafluoroethylene polymer coated magnetic stirring bar.

* * * * *